(12) United States Patent
Vanquickenborne

(10) Patent No.: US 10,555,908 B2
(45) Date of Patent: Feb. 11, 2020

(54) DOSAGE FORM ARTICLES FOR DELAYED RELEASE

(71) Applicant: Capsugel Belgium NV, Bornem (BE)

(72) Inventor: Stefaan Jaak Vanquickenborne, Rijmenam (BE)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 15/523,669

(22) PCT Filed: Nov. 24, 2015

(86) PCT No.: PCT/EP2015/077433
§ 371 (c)(1),
(2) Date: May 1, 2017

(87) PCT Pub. No.: WO2016/087263
PCT Pub. Date: Jun. 9, 2016

(65) Prior Publication Data
US 2017/0312227 A1     Nov. 2, 2017

(30) Foreign Application Priority Data

Dec. 2, 2014    (EP) .................................. 14195786

(51) Int. Cl.
*A61K 9/48*     (2006.01)
*A61J 3/07*     (2006.01)

(52) U.S. Cl.
CPC ............. *A61K 9/4808* (2013.01); *A61J 3/071* (2013.01); *A61J 3/074* (2013.01); *A61K 9/4816* (2013.01); *A61K 9/4833* (2013.01)

(58) Field of Classification Search
None
See application file for complete search history.

(56) References Cited

U.S. PATENT DOCUMENTS

| 1,815,902 | A | 7/1931 | Ellzey | |
|---|---|---|---|---|
| 2005/0008690 | A1 | 1/2005 | Miller | |
| 2010/0209389 | A1* | 8/2010 | McInnes | A61J 3/071 424/85.4 |
| 2012/0288562 | A1 | 11/2012 | Cade et al. | |
| 2014/0227357 | A1* | 8/2014 | Vertommen | A61K 9/4808 424/456 |

FOREIGN PATENT DOCUMENTS

| DE | 2729068 | 1/1979 |
|---|---|---|
| EP | 0861061 | 5/2002 |
| EP | 1117386 | 12/2004 |
| EP | 1301178 | 1/2007 |
| EP | 1942878 | 7/2008 |
| EP | 2211820 | 5/2012 |
| EP | 2777802 | 9/2017 |
| NL | 7610038 | 3/1978 |
| WO | WO2009/050646 | 4/2009 |

OTHER PUBLICATIONS

International Search Report and Written Opinion for PCT/EP2015/077433, dated Jan. 27, 2016.
International Preliminary Report on Patentability for PCT/EP2015/077433 (dated Jun. 15, 2017).

* cited by examiner

*Primary Examiner* — David J Blanchard
*Assistant Examiner* — Daniel F. Coughlin
(74) *Attorney, Agent, or Firm* — Klarquist Sparkman, LLP

(57) ABSTRACT

A comestible dosage form article for administration to a target subject, the dosage form comprising: an outer capsule comprising a first cap telescopically engageable with a first body; and an inner capsule, within the outer capsule, comprising a second cap telescopically engageable with a second body, wherein the inner capsule is inverted with respect to the outer capsule such that, in an assembled state, the second cap is proximal to the first body and distal to the first cap.

13 Claims, 1 Drawing Sheet

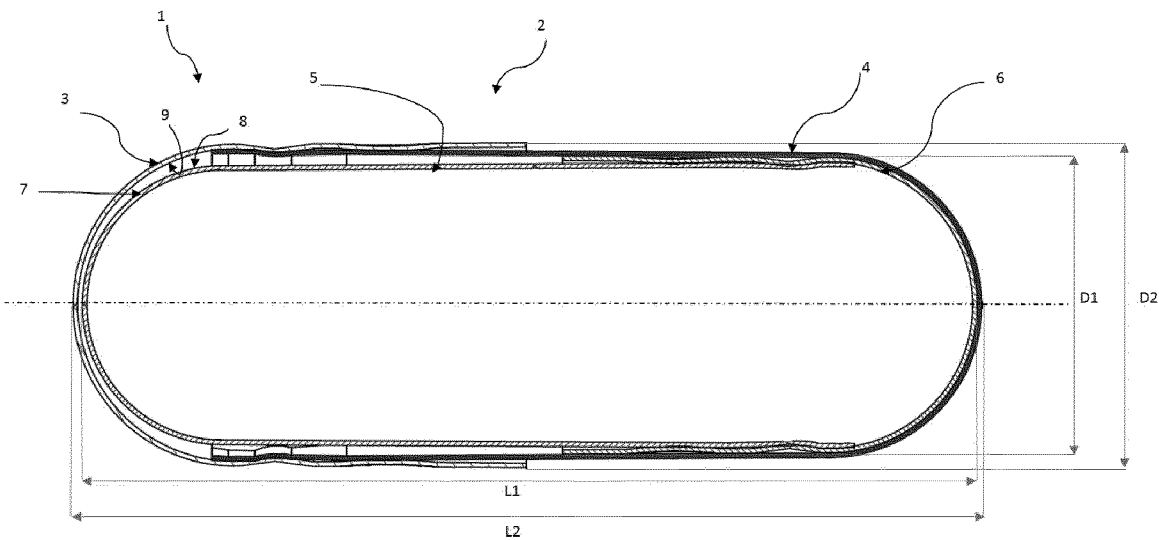

DOSAGE FORM ARTICLES FOR DELAYED RELEASE

CROSS REFERENCE TO RELATED APPLICATIONS

This is the U.S. National Stage of International Application No. PCT/EP2015/077433, filed Nov. 24, 2015, which in turn claims the benefit of and priority to European Patent Application No. 14195786.0, filed Dec. 2, 2014.

FIELD

The present disclosure relates to ingestible dosage form articles, preferably multi-part capsules, suitable for the delivery of one or more drugs. More particularly, the dosage form articles are suitable for ingestion by a subject, preferably the subject being selected from humans or animals.

BACKGROUND

Capsule technology continues to be subject to development and improvements. In its basic form, standard containers for pharmaceuticals or other powdered, granular or liquid substances (generally referred to as telescope-type or two-piece capsules) include a tubular-shaped and/or cylindrically-shaped first part, namely a cap part, which is closed on one end and open on the other opposite end. A tightly fitting second part of similar shape, namely the body part, is of smaller diameter than the cap part and is typically telescopically engaged therein to form the overall dosage form or two-piece capsule. Similar capsule technology may be used to generate multi-compartment capsules.

Delayed release in capsule technology is highly desirable since it permits to store within the capsule active materials that are normally acid instable and/or cause unpleasant side effects when reacting at stomach pH.

A number of ways for improving acid resistance of capsules have been described in the literature.

For example, EP111738661, describes a coated hydroxypropyl methylcellulose (HPMC) comprising capsule with delayed release properties.

US2012/288562A1 as further example, describes an acid resistance capsule for delayed release by forming a capsule shell of an HPMC comprising material in combination with a gelling aid in order to provide such delayed release without additional coating of the capsule being necessary.

Aside from coating and capsule shell formulations, other methods of improving delayed release of capsules has been achieved by banding capsules on the juncture between capsule cap and capsule body, as exemplified in EP1942878A2.

Although, acid resistance and delayed release has been successfully improved over time via formulation specific developments, including by surface modification and/or by capsule shell composition, a need still remains to further develop a capsule design/shape that by nature of its design further aids delayed release.

In terms of capsule design, the known dosage forms may be classified in two distinct design types: the first comprise mono-compartment dosage forms, the second comprises multi-compartment dosage forms.

Known single (or mono) compartment dosage forms are typically in the form of classic two-piece capsules comprising a body and a cap, as described for example in EP086106161. In the context of delayed release, these designs however do not further improve delayed release since there is a single "wall"/shell that must be dissolved before the active stored therein is released.

Multi-compartment dosage forms are known and are generally used for storing one or more incompatible components therein.

Some multi-compartment dosage forms are in the form of multiple two-piece capsules stored within one another. Generally this involves a larger two-piece capsule forming the outer shell of the dosage form and one or more smaller two-piece capsules therein storing different mediums therein. An example of this arrangement is described in EP1301178B1. Disadvantages of this arrangement include dislocation of the inner capsules with respect to the outer capsule which may result in damage of the content and/or capsules themselves during handling, overall size limitations of the dosage form, and large spacing/compartment between the inner and outer capsules.

Other multi-compartment dosage forms, such as described in EP2211820B1, are in the form of two-piece capsules with a main cap and a main body being joined to form a first compartment and a further body joined to the outer surface of the aforementioned main body to form a second compartment. Disadvantages of this arrangement include increased overall volume size of the dosage form (particularly overall length of the same) which may be undesirable for swallowability, risk of premature disengagement of the further body from the main body with subsequent spill of the content during handling, as well as requiring complex filling processes in order to fill and assemble the final product. In the context of delayed release, also such arrangements fail to bring added benefits because only a single "wall"/shell must be dissolved before the active stored therein is released.

Therefore there still remains a need for a dosage form article that overcomes the problems of the prior art and in particular allows for effectively improving delayed release of its contents whilst minimizing overall size of the dosage form and maximizing the amount of useful actives that can be stored therein.

SUMMARY

A first aspect of the present disclosure relates to a comestible dosage form article for administration to a target subject, the dosage form comprising: an outer capsule comprising a first cap telescopically engageable with a first body; and an inner capsule, within the outer capsule, comprising a second cap telescopically engageable with a second body, wherein the inner capsule is inverted with respect to the outer capsule such that, in an assembled state, the second cap is proximal to the first body and distal to the first cap.

A further aspect of the present disclosure relates to methods of filling the same and uses thereof.

BRIEF DESCRIPTION OF THE DRAWINGS

FIG. 1 is an illustration of a cross-sectional view of a dosage form article according to one aspect of the disclosure.

DETAILED DESCRIPTION

By the term "a" and/or "an" when describing a particular element, it is intended "at least one" of that particular element.

By the term "medicament", it is intended a "drug" or the like comprising one or more compounds providing one or more curative benefits to a subject, the terms "medicament" and "drug" may be used interchangeably herein.

By the term "hard shell" or "hard capsule shell", it is intended a shell that is deformable, but which returns to its un-deformed shape upon the removal of a deforming force. Typically such shells comprise, for example, less than 25%, preferably less than 20%, more preferably from 0% to 14%, even more preferably from greater than 0% to less than 14%, water by weight.

By the term "compartment", it is intended as a definite volume for storing a drug therein, such volume typically being formed and delimited by multiple parts (i.e. a plurality of distinct segments) when connected to each other.

By the term "multiple parts" or "plurality of distinct segments", it is intended the portions making up the dosage form article which, when connected, form one or more compartments. Such portions are separate components and typically comprise, preferably consist of, cap part(s), body part(s), and combinations thereof.

By the term "enteric release", it is intended that the dosage form articles herein do not leak at pH 1.2 in a USP-30 simulated gastric fluid for at least 2 hours, preferably at least 2.5 hours.

Various embodiments will now be described to provide an overall understanding of the principles of the structure, function, manufacture, and use of dosage form articles and methods disclosed herein. One or more examples of these embodiments are illustrated in the accompanying figures. Those of ordinary skill in the art will immediately understand that features described or illustrated in connection with one example embodiment can be combined with the features of other example embodiments without generalization from the present disclosure.

Dosage Form Articles

Referring to FIG. 1, the disclosure herein relates to a comestible dosage form article 1 for administration to a target subject, the dosage form comprising: an outer capsule 2 comprising a first cap 3 telescopically engageable with a first body 4; and an inner capsule 5, within the outer capsule 2, comprising a second cap 6 telescopically engageable with a second body 7. The inner capsule 5 is inverted with respect to the outer capsule 2 such that, in an assembled state, the second cap 6 is proximal to the first body 4 and distal to the first cap 3. This arrangement has the advantage of maximizing the size of the inner capsule whilst at the same time avoiding processing issues that may particularly result during the insertion of the inner capsule into the body of the outer capsule (e.g. inadvertent opening of the inner capsule and/or deformation of the capsule upon rim-to-rim contact). This is particularly desirable when attempting to minimize as much as possible the size of the dosage from articles whilst still providing a sufficiently large inner capsule volume for incorporating a sufficiently large amount of medicament therein.

In an embodiment, the inner capsule 5, preferably only the inner capsule, comprises a medicament therein, preferably wherein the medicament is acid instable. In this arrangement the inner capsule is the only compartment of the dosage form suitable for retaining an active substance therein.

In a preferred embodiment, the outer and inner capsules 2, 5 are sized such that substantially no compartment is present between the inner and outer capsule 2, 5. An advantage of this arrangement is to essentially provide a single compartment dosage form that minimizes the gap between the inner and outer capsule such that there is no useful space for filling a substance therein.

In an embodiment (not shown), at least the outer capsule 2 comprises a first cap 3 telescopically engageable with a first body 4 and arranged such that, in the assembled state, the first cap 3 extends over the first body 4 and along substantially the whole length of the first body 4 typically up to a position proximal to the closed end of the first body 4. The same arrangement may be applied to the inner capsule 5 (with respective second cap and body arranged in the same manner as described above). Advantages of this arrangement include the possibility of effectively increasing the number of capsule layers between the fill contents of the inner capsule (e.g. the medicament) and the outside environment across substantially the whole length of the capsule. It is apparent, for example, that inversion of the inner capsule results in a 3-wall configuration in the cap/body overlap region (and on a portion of the total capsule length), and by increasing the length of the first cap of the outer capsule the result is an at least 3-wall configuration along substantially the entire length of the capsule. It goes without saying that by doing the same to the inner capsule the result is in a 4-wall configuration along substantially the entire length of the capsule. Increasing the number of inner capsules would then proportionally increase the number of walls and thus controlled or delayed release benefits. Without wishing to be bound by theory, it is believed that such arrangements provide for better and more homogenous controlled release and dissolution.

The dosage form articles herein may be in the form of one or more hard capsules, the assembly of which (i.e. the totality of capsules), comprises a single compartment, typically for retaining a predetermined dose of a substance comprising a medicament.

An outer surface 8 of the inner capsule 5 may be in contact with an inner surface 9 of the outer capsule 2. Preferably more than one outer surfaces of the inner capsule is in contact with more than one inner surface of the outer capsule. More preferably all outer surfaces of the inner capsule may contact or be in contact with all the inner surface of the outer capsule.

In an embodiment, the outer and inner capsules 2, 5 are made of the same or different materials, preferably the same materials. The material may comprise any material known in the art for making hard capsules such as gelatin (bovine, porcine or fish source), polymers (such as cellulose derivatives, polysaccharides, polyacrylates and the like). Preferably however, the material comprises one or more acid resistant and/or enteric materials, typically selected from the group consisting of hydroxypropyl methylcellulose (HPMC), cellulose acetate phthalate (CAP), hydroxypropyl methylcellulose acetate succinate (HPMCAS), and mixtures thereof.

In an embodiment, both inner and outer capsules 2, 5 are made of a shell material comprising a combination of hydroxypropyl methylcellulose (HPMC) and gellan gum.

In an embodiment, the inner and/or outer capsules are selected from HPMC-based capsules (such as Vcaps® or Vcaps Plus® capsules supplied by CAPSUGEL®), pullulan-based capsules (such as Plantcaps® capsules supplied by CAPSUGEL®), HPMC/Gellan-based capsules (such as DRcaps® capsules supplied by CAPSUGEL®), gelatin-based capsules (such as Coni-Snap® capsules supplied by CAPSUGEL®), and combinations thereof. It is apparent that by different combination of such capsules as inner/outer capsules different controlled and target release profiles may be achieved depending on the desired release characteristics and materials to be filled in the capsule.

In a preferred embodiment, at least the outer capsule 5 is banded, preferably wherein both inner and outer capsules 2, 5 are banded. Any suitable banding composition may be used, for example HPMC-based aqueous banding compositions comprising one or more surfactants, and/or organic solvents. Further banding the dosage forms herein aid in providing even further delayed release.

In an embodiment, the second body 7 and/or second cap 6 are elongate in shape and are sized such that when assembled, the overall length ratio L1/L2 of the inner capsule 5 to outer capsule 2 is from 0.80 to less than 1, preferably from 0.85 to less than 1, more preferably from 0.9 to 0.99, even more preferably from 0.95 to 0.99. The lengths L1 and L2 are typically taken from one end of the respective assembled capsule body to the end of the respective cap (typically at the apex of each respective dome shaped closed end). In this arrangement, the body and/or cap are projected longer than traditional caps and bodies used in the art, particularly for maximizing the volume of the inner capsule and minimizing the volume between the inner and outer capsules.

In an embodiment, the second body 7 and/or second cap 6 are sized such that when assembled, the overall diameter ratio D1/D2 of the inner capsule 5 to outer capsule 2 is from 0.75 to less than 1, preferably from 0.80 to 0.99, more preferably from 0.90 to 0.99. The diameters D1 and D2 are typically measured at the region of overlap between the respective capsule body and cap taking the measurement between end-to-end outer surfaces of respective caps.

It is understood herein that a plurality of inner capsules may be comprised in the dosage form articles described herein following the same relationships and features described in embodiments herein above. The medicament is nevertheless typically stored in the innermost capsule of the dosage form article.

Drug/Medicament

Drugs (i.e. medicaments) suitable for use in the dosage form articles described herein may take any form and be for any treatment of a human or animal subject. This includes not only pharmaceutical compounds but also dietary supplements such as vitamins, minerals and the like.

The drug may be in a state selected from solid or liquid, preferably solid, at room temperature and atmospheric pressure, and comprises one or more active compounds.

Suitable compounds (and generally encompassed by the term "medicament" as used herein) for delivery according to the disclosure include, but are not limited to, particulate, powder, waxy, liquid, and/or pellet forms of the following:

a) pharmaceuticals (also called pharmaceutical actives) such as betamethasone, thioctic acid, sotalol, salbutamol, norfenefrine, silymahn, dihydroergotamine, buflomedil, etofibrate, indomethacin, oxazepam, acetyldigitoxins, piroxicam, halopehdol, isosorbide mononitrate, amithptyline, diclofenac, nifedipine, verapamil, pyritinol, nitrendipine, doxy-cycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovir-mononitrate, paracetamolol, naftidrofuryl, pentoxifylline, propafenone, acebutolol, 1-thyroxin, tramadol, bromocriptine, loperamide, ketofinen, fenoterol, ca-dobesilate, propranolol, minocycline, nicergoline, ambroxol, metoprolol, B-sitosterin, enalaprilhydro-genmaleate, bezafibrate, isosorbide dinitrate, gallopamil, xantinolnicotinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclo-pramide, acemetacin, ranitidine, biperiden, metamizol, doxepin, dipotassiumchloraze-pat, tetrazepam, estramustinephosphate, terbutaline, captopril, maprotiline, prazosin, atenolol, glibenclamid, cefaclor, etilefrin, cimetidine, theophylline, hydromorphone, ibu-profen, prim idone, clobazam, oxaceprol, medroxyprogesterone, flecainide, Mg-pyhdoxal-5-phosphateglutaminate, hymechromone, etofyllineclofibrate, vincamine, cin-narizine, diazepam, ketoprofen, flupentixol, molsidomine, glibornuhde, dimethindene, melperone, soquinolol, dihydrocodeine, clomethiazole, clemastine, glisoxepid, kallidino-genase, oxyfedhne, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitriptyline, caproteron, sodium valproinate, mebeverine, bisacodyl, 5-amino-salicyclic acid, dihydralazine, magaldrate, phenprocou-mon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, [beta]-carotene, cloramphenicol, chlorodiazepoxid, chlormadinoneacetate, chlorothiazide, cin-narizine, clonazepam, codeine, dexamethasone, dicumarol, digoxin, drotaverine, grami-cidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbi-tal, phenylbutazone, phenytoin, prednisone, reserpine, spironolactine, streptomycin, sul-famethizole, sulfamethazine, sulfamethoxazole, sulfamethoxydiazinon, sulfathiazole, sulfisoxazole, testosterone, tolazamide, tolbutamide, trimethoprim, tyrothricin, antacids, reflux suppressants, antiflatulents, antidopaminergics, proton pump inhibitors, H2-receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, ACE inhibitors, angiotensin receptor blockers, alpha blockers, anticoagulants, heparin, antiplatelet drugs, fibrinolytic, anti-hemophilic factor, haemostatic drugs, hypolipidaemic agents, statins, hypnotics, anaesthetics, antipsychotics, antidepressants (including tricyclic antidepressants, monoamine oxidase inhibitors, lithium salts, selective serotonin reuptake inhibitors), anti-emetics, anticonvulsants, an-tiepileptics, anxiolytics, barbiturates, movement disorder drugs, stimulants (including amphetamines), benzodiazepine, cyclopyrrolone, dopamine antagonists, antihistamines, cholinergics, anticholinergics, emetics, cannabinoids, 5-HT antagonists, analgesics, muscle relaxants, antibiotics, sulfa drugs, aminoglycosides, fluoroquinolones, bronchodilators, NSAIDs, anti-allergy drugs, antitussives, mucolytics, decongestants, corticosteroids, beta-receptor antagonists, anticholinergics, steroids, androgens, antian-drogens, gonadotropin, corticosteroids, growth hormones, insulin, antidiabetic drugs (including sulfonylurea, biguanide/metformin, and thiazolidinedione), thyroid hormones, antithyroid drugs, calcitonin, diphosponate, vasopressin analogs, contraceptives, follicle stimulating hormone, luteinising hormone, gonadotropin release inhibitor, progestogen, dopamine agonists, oestrogen, prostaglandin, gonadorelin, clomiphene, tamoxifen, di-ethylstilbestrol, antimalarials, anthelmintics, amoebicides, antivirals, antiprotozoals, vaccines, immunoglobulin, immunosuppressants, interferon, monoclonal antibodies, and mixtures thereof;

b) vitamins, e.g., fat-soluble vitamins such as vitamins A, D, E, and K, and water soluble vitamins such as vitamin C, biotin, folate, niacin, pantothenic acid, riboflavin, thiamin, vitamin B6, vitamin B12, and mixtures thereof;

c) minerals, such as calcium, chromium, copper, fluoride, iodine, iron, magnesium, manganese, molybdenum, phosphorus, potassium, selenium, sodium (including sodium chloride), zinc, and mixtures thereof;

d) dietary supplements such as herbs or other botanicals, amino acids, and substances such as enzymes, organ tissues, glandulars, and metabolites, as well as concentrates, metabolites, constituents, extracts of dietary ingredients, oils such as krill oil and mixtures thereof;

e) homoeopathic ingredients such as those listed in the Homeopathic Pharmacopoeia of the United States Revision Service (HPRS), and mixtures thereof. It must be recognized, of course, that the HPRS is periodically updated and that the present invention includes homeopathic ingredients that may be added to the HPRS;

f) probiotics and yeast, such as bacteria selected from the group consisting of *Lactobacillus* (Döderlein's bacilli) such as *Lactobacillus crispatus, Lactobacillus jensinii, Lactobacillus johnsonii, Lactobacillus gasseri, Enterococcus faecium*, or fungi selected from the group of Saccharomycetales such as *Saccharomyces boulardii*.

g) hormones, such as estrogen (i.e. a natural estrogen or a synthetic compound that mimics the physiological effect of natural estrogens) including, without limitation, estradiol (17-estradiol), estridiol acetate, estradiol benzoate, estridiol cypionate, estridiol decanoate, estradiol diacetate, estradiol heptanoate, estradiol valerate, 17a-estradiol, estriol, estriol succinate, estrone, estrone acetate, estrone sulfate, estropipate (piperazine estrone sulfate), ethynylestradiol (17a-ethynylestradiol, ethinylestradiol, ethinyl estradiol, ethynyl estradiol), ethynylestradiol 3-acetate, ethynylestradiol 3-benzoate, mestranol, quinestrol, nitrated estrogen derivatives or combinations thereof; or progestin (i.e. natural or synthetic compounds that possesses progestational activity including, without limitation, nortestosterone, ethynyltestosterone, deacetylnorgestimate, hydroxyprogesterone, 19-norprogesterone, 3P-hydroxydesogestrel, 3-ketodesogestrel (etonogestrel), acetoxypregnenolone, algestone acetophenide, allylestrenol, amgestone, anagestone acetate, chlormadinone, chlormadinone acetate, cyproterone, cyproterone acetate, demegestone, desogestrel, dienogest, dihydrogesterone, dimethisterone, drospirenone, dydrogesterone, ethisterone (pregneninolone, 17a-ethynyltestosterone), ethynodiol diacetate, fluorogestone acetate, gastrinone, gestadene, gestodene, gestonorone, gestrinone, hydroxymethylprogesterone, hydroxymethylprogesterone acetate, hydroxyprogesterone, hydroxyprogesterone acetate, hydroxyprogesterone caproate, levonorgestrel (1-norgestrol), lynestrenol (lynoestrenol), mecirogestone, medrogestone, medroxyprogesterone, medroxyprogesterone acetate, megestrol, megestrol acetate, melengestrol, melengestrol acetate, nestorone, nomegestrol, norelgestromin, norethindrone (norethisterone) (19-nor-17a-ethynyltestosterone), norethindrone acetate (norethisterone acetate), norethynodrel, norgestimate, norgestrel (d-norgestrel and dl-norgestrel), norgestrienone, normethisterone, progesterone, promegestone, quingestanol, tanaproget, tibolone, trimegestone, or combinations thereof.
and mixtures in any combination of the foregoing.

In a preferred embodiment, the medicament is acid instable. The term "acid instable" as used herein typically means substances that tend to react and/or decompose at low pH, typically pH less than 6, including substances associated with gastric side effects in humans and/or animals. Non-limiting examples of such substances include enzymes, bacteria such as bifidobacteria, certain dietary supplements such as valerian root, garlic, and the like.

Methods and Uses

Dosage form articles describe herein are particularly useful for delayed release of a medicament stored therein, preferably wherein said delayed release is an enteric release. The particular design of such dosage forms ensures that a predetermined dose is released enterically whilst at the same time maximizing the dose of medicament and limiting the overall size of the dosage form. The latter affects effectiveness of the desired treatment as well as patient acceptance by allowing ease of swallowing (particularly advantageous for applications including administration to children and elderly subjects, and/or subjects with swallowing issues).

Methods of filling a dosage form article herein typically comprise the steps of: providing a first body 4; providing an inner capsule 5 having a second cap 6 and a second body 7, preferably filled with a substance comprising a medicament; re-orienting the inner capsule 5 such that the second cap 6 thereof is capable of being inserted into said first body 4; inserting said inner capsule 5 into said first body 4; inserting a first cap 3 over the first body 4 such to close the dosage form article 1 with the inner capsule 5 therein. Preferably, wherein at least a portion of the overlap region of the first cap 3 and first body 4 is banded with a banding composition, preferably wherein the inner capsule 5 is filled, closed, and banded prior to the insertion step into the first body 4. Advantages of such methods include ease of in-line filling of dosage form articles with maximized inner capsule size and outer capsule reduction, whilst limiting risk of accidental opening, particularly during the capsule insertion step, and/or deformation (or even failure) of the capsule parts.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" (i.e. every value in a practical range close to 40 mm).

The invention claimed is:

1. A comestible dosage form article for administration to a target subject, the dosage form comprising:
   an outer capsule comprising a first cap telescopically engageable with a first body; and
   an inner capsule, within the outer capsule, comprising a second cap telescopically engageable with a second body,
   the inner capsule being in an inverted position with respect to the outer capsule such that, in an assembled state, the second cap is proximal to the first body and distal to the first cap;
   wherein the outer and inner capsules are sized such that substantially no compartment is present between the inner and outer capsule.

2. A dosage form article according to claim 1 wherein the inner capsule further comprises a medicament therein.

3. A dosage form article according to claim 1 wherein the dosage form article is a hard capsule comprising a single compartment configured to retain a predetermined dose of a substance comprising a medicament.

4. A dosage form article according to claim 1 wherein an outer surface of the inner capsule is in contact with an inner surface of the outer capsule.

5. A dosage form article according to claim 1 wherein the outer and inner capsules are made of the same materials.

6. A dosage form article according to claim 5 wherein the material comprises one or more acid resistant and/or enteric materials comprising hydroxypropyl methylcellulose (HPMC), cellulose acetate phthalate (CAP), hydroxypropyl methylcellulose acetate succinate (HPMCAS), or any mixture thereof.

7. A dosage form article according to claim 1 wherein both inner and outer capsules are made of a shell material comprising a combination of hydroxypropyl methylcellulose (HPMC) and gellan gum.

8. A dosage form article according to claim 1 wherein at least the outer capsule is arranged such that the first cap extends over and along the first body and substantially over the whole length thereof up to a position proximal to a closed end of said first body.

9. A dosage form article according to claim 1 wherein at least the outer capsule is banded.

10. A dosage form article according to claim 1 wherein the second body and/or second cap are elongate in shape and are sized such that when assembled, the overall length ratio (L1/L2) of the inner capsule to outer capsule is from 0.80 to less than 1.

11. A dosage from article according to claim 1 wherein the second body and/or second cap are sized such that when assembled, the overall diameter ratio (D1/D2) of the inner capsule to outer capsule is from 0.75 to less than 1.

12. A method of filling a dosage form article comprising:
  providing an outer capsule comprising a first cap telescopically engageable with a first body;
  providing an inner capsule, the inner capsule comprising a second cap telescopically engageable with a second body;
  inserting the inner capsule being in an inverted position with respect to the outer capsule such that, in an assembled state, the second cap is proximal to the first body and distal to the first cap; and
  wherein the outer and inner capsules are sized such that substantially no compartment is present between the inner and outer capsule.

13. A method according to claim 12 wherein at least a portion of the overlap region of the first cap and first body is banded with a banding composition, and is banded prior to the inserting the first cap over the first body.

* * * * *